US012714513B2

(12) United States Patent
Ivan et al.

(10) Patent No.: US 12,714,513 B2
(45) Date of Patent: Aug. 25, 2026

(54) AUGMENTED AND MIXED REALITY INCORPORATING PATHOLOGY RESULTS IN SURGICAL SETTINGS

(71) Applicant: University of Miami, Miami, FL (US)

(72) Inventors: Michael E. Ivan, Miami, FL (US); Max Cacchione, Miami, FL (US); Adam McMahon, Ft. Lauderdale, FL (US)

( * ) Notice: Subject to any disclaimer, the term of this patent is extended or adjusted under 35 U.S.C. 154(b) by 0 days.

(21) Appl. No.: 18/720,585

(22) PCT Filed: Dec. 16, 2022

(86) PCT No.: PCT/US2022/053159

§ 371 (c)(1),
(2) Date: Jun. 14, 2024

(87) PCT Pub. No.: WO2023/114470

PCT Pub. Date: Jun. 22, 2023

(65) Prior Publication Data

US 2025/0082411 A1 Mar. 13, 2025

Related U.S. Application Data

(60) Provisional application No. 63/290,179, filed on Dec. 16, 2021.

(51) Int. Cl.
*A61B 5/05* (2021.01)
*A61B 34/10* (2016.01)
(Continued)

(52) U.S. Cl.
CPC .............. *A61B 34/20* (2016.02); *A61B 34/10* (2016.02); *A61B 90/37* (2016.02); *G16H 30/20* (2018.01);
(Continued)

(58) Field of Classification Search
CPC ... A61B 34/20; A61B 34/10; A61B 2034/105; A61B 2034/2055; A61B 2090/364
See application file for complete search history.

(56) References Cited

U.S. PATENT DOCUMENTS

2014/0343404 A1* 11/2014 Razzaque ............ A61B 8/0841 600/424
2016/0364630 A1* 12/2016 Reicher ................ G06T 7/0014
(Continued)

OTHER PUBLICATIONS

Extended European Search Report, European Patent Application No. 22908486.8, dated Nov. 17, 2025, 11 pages.

*Primary Examiner* — Joel F Brutus
(74) *Attorney, Agent, or Firm* — Fitch, Even, Tabin & Flannery LLP

(57) ABSTRACT

Apparatuses and methods for using augmented/mixed reality in surgical settings are provided, and, in particular, apparatuses and methods for intraoperative integration of augmented/mixed reality 3D models with near real-time pathology results. Real-time pathology results are generated using a machine learning analysis of biopsy pathology images in conjunction with a predictive model based on the patient's clinical and demographic data and radiographic imaging data. The apparatuses and methods can be used to provide more accurate intraoperative visualization, tracking, and determination of tumor margins to improve resection extent and any intraoperative or postoperative adjuvant therapy.

20 Claims, 8 Drawing Sheets

(51) Int. Cl.

| | |
|---|---|
| ***A61B 34/20*** | (2016.01) |
| ***A61B 90/00*** | (2016.01) |
| ***G16H 30/20*** | (2018.01) |

(52) U.S. Cl.

CPC . *A61B 2034/105* (2016.02); *A61B 2034/2055* (2016.02); *A61B 2090/364* (2016.02)

(56) References Cited

U.S. PATENT DOCUMENTS

| | | | | |
|---|---|---|---|---|
| 2018/0116732 | A1* | 5/2018 | Lin | A61B 34/20 |
| 2021/0022812 | A1 | 1/2021 | Tako et al. | |
| 2021/0153943 | A1 | 5/2021 | Piron et al. | |
| 2021/0375457 | A1* | 12/2021 | LeBoeuf | G06N 3/0464 |

* cited by examiner

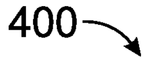

470 Coordinates of a marked point indicating the location of a tissue removal/biopsy sample in the 3D model of the area of interest are sent to the server, and the marked point is represented as a marker in a neutral color (e.g., gray) in the AR/VR representation 475 The server outputs a pathology result for the tissue removal/biopsy sample to the AR/VR headset 480 The marked point in the 3D model of the area of interest is updated with the result and the marker is color-coded in the AR/VR representation based on the pathology result (e.g., based on tumor probabilities such as cancer presence, recurrence, or time to recurrence)

485 The surface of the 3D model of the area of interest is updated: for every updated marker a list in the program containing these markers is updated to reflect the points that are on the surface of the shape so that the shape of the 3D model of the area of interest can be updated 490 The 3D mesh is updated: from the points on the surface of the shape, triangles are created to form the updated 3D mesh of the area of interest

FIG. 4

AUGMENTED AND MIXED REALITY INCORPORATING PATHOLOGY RESULTS IN SURGICAL SETTINGS

CROSS REFERENCE TO RELATED APPLICATIONS

This application is a U.S. national stage application of International Application No. PCT/US2022/53159, filed Dec. 16, 2022, designating the United States, which claims priority to U.S. Provisional Application No. 63/290,179, filed on Dec. 16, 2021, the contents of which are incorporated herein by reference in their entirety for all purposes.

FIELD

The apparatuses and methods described herein relate generally to the use of augmented and mixed reality in surgical settings and, more particularly, to the use of augmented and mixed reality and pathology analysis to guide surgical resections by providing intraoperative visualization and determination of tumor margins as well as collect intraoperative data for future treatment planning.

BACKGROUND

Resection is often used to treat tumors and other abnormal tissue throughout the body and involves the surgical removal of the tumor or tissue. Ensuring that a tumor has been completely or sufficiently removed during a resection is especially critical with respect to cancer, since residual malignant cells after resection are likely to cause cancer recurrence.

In practice, however, successful removal of a tumor is challenging. This is particularly the case with respect to cranial neurosurgical resection. Brain tumors exist within the context of complex neural networks, making it difficult to differentiate microscopic tumor tissues from normal tissues during surgery. As such, neurosurgeons struggle to track the boundary of a tumor during surgery and accurately determine safe tumor margins, that is, the margins of non-tumorous or healthy tissue surrounding a tumor to be removed along with the tumor to mitigate risk of any tumor being left behind. The limitations surgeons face in accurately visualizing and determining tumor margins during surgery leads to incomplete, imprecise resection, and ultimately to worse patient outcomes.

Current intraoperative strategies for identifying tumor margins have drawbacks. For example, during surgery, tumor cells can be identified on a microscopic level by frozen section analysis of margin samples. Frozen section analysis, however, is a time- and labor-intensive process, and thus cannot provide the rapid assessment of numerous margin samples needed to provide actionable guidance for determining precise tumor margins as the surgeon operates. Some forms of fluorescence-guided surgery can provide more rapid detection of tumor tissue; however, fluorescence-guided surgery has low specificity, can only be used for high grade gliomas cancer type, and offers only macroscopic visibility.

SUMMARY

In the most general aspect, described herein are apparatuses and methods for using augmented and mixed reality in surgical settings. In particular, and advantageously, the apparatuses and methods provide accurate intraoperative visualization, tracking, and determination of tumor margins via a seamless integration of augmented and mixed reality 3D models and navigation with visualization of near real-time pathology results. The pathology results can also be stored as geo-tagged data relative to an image or model of a patient's anatomy to be used for guiding future targeted treatment and disease monitoring.

Generally, an apparatus described herein includes an integrated network including a computer system; an augmented/mixed reality device, including augmented/mixed reality software and hardware, operable to generate and display a 3D model of a patient's anatomy in a surgical field to a user of the device based on data from a pathology machine operable to rapidly determine pathology results of biopsy samples using artificial intelligence (AI), wherein the pathology results are used to update the 3D model during surgery and are displayed to the user in the surgical field; and a central server operable to store data, communicate with the augmented/mixed reality device and pathology machine, and perform one or more processes associated with the augmented reality device and pathology machine. The 3D model may then be converted to Communications in Medicine ("DICOM images") that include geo-tagged pathology information, and the images used to guide future postoperative care, for example, to target areas of tumor residual with adjuvant treatment such as radiation.

In embodiments, the apparatus also includes one or more machine learning models that analyze pathology results to provide near real-time information during surgery. For instance, a machine learning model may be employed that examines high resolution images of the biopsies outputted by the pathology machine. Additionally, a machine learning model may be employed to consider a patient's demographic and clinical data (age, ethnicity, clinical history, gender, nutrition, ethnicity, trauma, past surgeries, geographic data, etc.) and the updated 3D model to determine or predict a probability of cancer presence, recurrence, and/or time to recurrence for the patient generally or associated with the biopsy sample location. The probability may be displayed to the user in the surgical field and may be used to further update the 3D model. By one approach, an apparatus for providing intraoperative and postoperative surgery guidance provided herein includes a computer system operable to generate a 3D model of an area of interest on a patient's body and a head-mounted augmented/mixed reality display device to be worn by a user, for generating a representation of the area of interest based on the 3D model of the area of interest displayed as an overlay over a user's view of the area of interest during a surgical operation, wherein the representation includes pathology characteristics associated with the area of interest. In some embodiments, the computer system includes a central server operable to communicate with the head-mounted augmented/mixed reality display device to detect a tissue removal and a section location associated with the tissue removal, associate the section location with a pathology result associated with the tissue removal in the 3D model of the area of interest to provide an updated 3D model of the area of interest, and, based on the pathology result, update an indicator associated with the section location of the tissue removal in the representation of the area of interest displayed on the head-mounted display device to provide an updated representation of the area of interest.

Generally, a method for using augmented and mixed reality in surgical settings, in particular a method in which pathology results are incorporated into augmented and mixed reality 3D models to guide surgery, includes uploading preoperative information including medical imaging files and other data relating to a patient (including clinical and/or demographic information) to a central server, and providing the information to an augmented/mixed reality device, which uses the information to generate an augmented/mixed reality 3D model of a patient's anatomy overlaid on the patient's body and registered thereto. So configured, accurate, continuous, real-time anatomical visualization and navigation is provided as a surgeon operates. In some embodiments, the method further includes collecting a tissue sample from a location; marking the location of the sample in the augmented/mixed reality model; providing the tissue sample to a pathology machine, which determines a pathology result using artificial intelligence and provides the pathology result to the central server; receiving the pathology result from the central server at the augmented/mixed reality device; and automatically updating the augmented/mixed reality model with the pathology result during surgery. The method may further include storing the pathology result and marked location on the central server and accessing or downloading the pathology result on a web portal. In a further aspect, pathology results accessed or downloaded from the central server are received as imaging files having a geolocational overlay of the pathology results, and the method includes a step of using the files to guide postoperative therapy. The files may be correlated to additional postoperative images to help identify areas of disease progression.

In embodiments, the method includes analyzing pathology results via one or more machine learning models to provide near real-time information during surgery. For instance, the method may include employing a machine learning model to examine high resolution images of the biopsies outputted by the pathology machine to determine a pathology result for updating the 3D model. Additionally, the method may employ a machine learning model to consider a patient's demographic and clinical data (age, ethnicity, clinical history, gender, nutrition, ethnicity, trauma, past surgeries, geographic data, etc.) and the updated 3D model to determine or predict a probability of cancer presence, recurrence, and time to recurrence for the patient generally or associated with the biopsy sample location. The method may include displaying the probability to the user in the surgical field and using the probability to further update the 3D model. A further step includes embedding the determined pathology information into DICOM image files converted from the 3D model and/or embedding the information into postoperative DICOM medical imaging. The DICOM files embedded with the pathology information can be stored on a server and accessed for future treatment planning and tumor/disease assessment. Further described herein are methods for providing intraoperative surgery guidance, methods for precisely determining tumor margins in a resection surgery using augmented or mixed reality incorporating near real-time pathology results, methods of using augmented/mixed reality software and a central server to automatically process a marked location and identification for a collected pathology sample, methods of automatically updating an augmented/mixed reality 3D tumor model depending on pathology sample results, and apparatuses for performing these various methods.

BRIEF DESCRIPTION OF THE DRAWINGS

FIG. 4 is a flow diagram of a method in which an augmented/mixed reality device and central server perform a process to incorporate near real-time pathology results into an augmented reality 3D model, in accordance with some embodiments.

DETAILED DESCRIPTION

Figure 1:
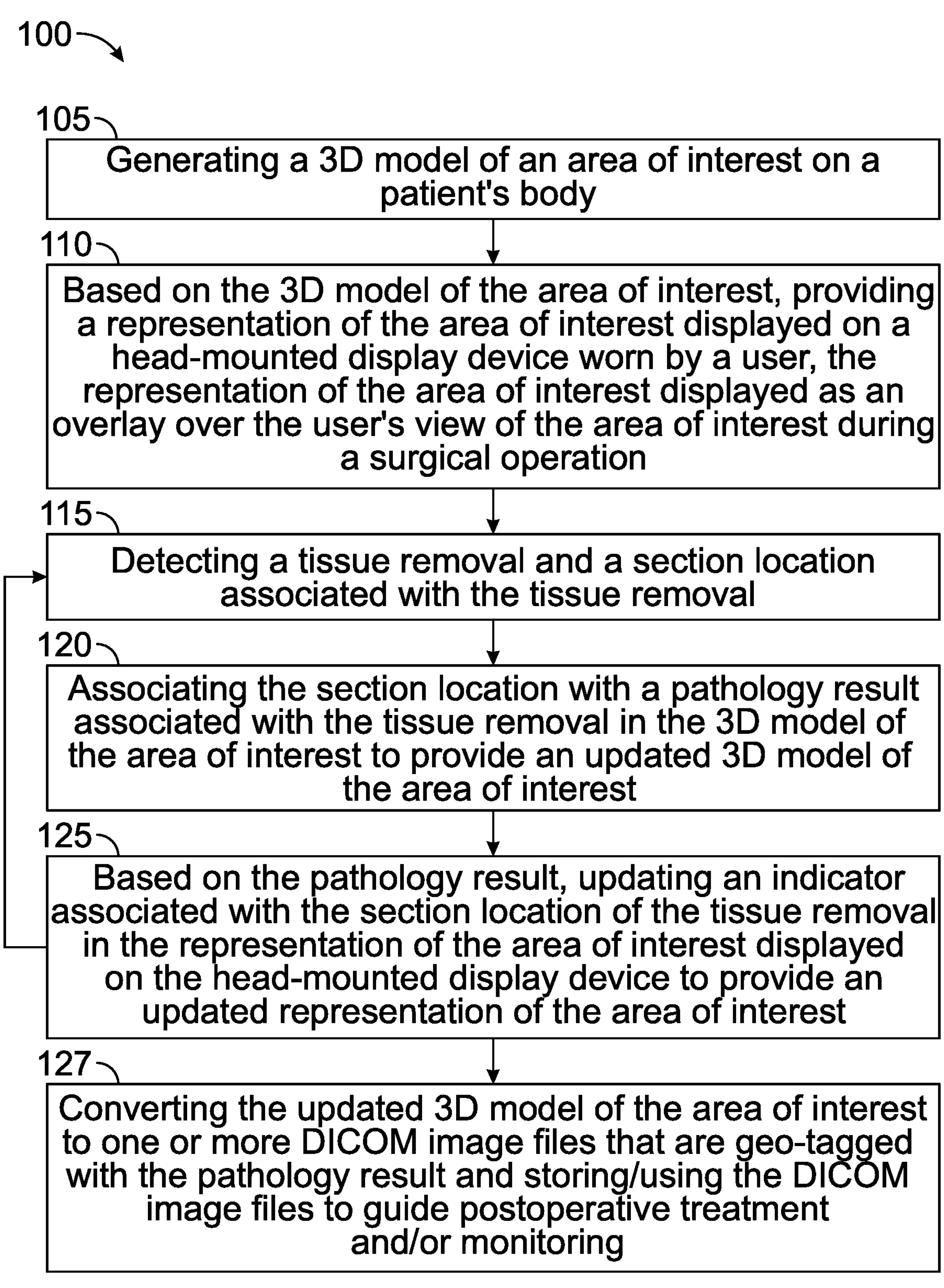
FIG. 1 is a flow diagram of a method for providing intraoperative surgery guidance, as well as postoperative guidance, in accordance with some embodiments.

In one approach, as shown in FIG. 1, a method 100 for providing intraoperative surgery guidance, as well as postoperative guidance, generally includes 105 generating a 3D model of an area of interest on a patient's body. A further step 110 includes using the 3D model of the area of interest to provide a representation of the area of interest displayed on a head-mounted display device worn by a user (such as a surgeon), the representation of the area of interest displayed as an overlay over the user's view of the area of interest during a surgical operation. During the surgery, 115 a tissue removal or sample is detected along with a section location associated with the tissue removal. At step 120, the section location is associated with a pathology result associated with the tissue removal within the 3D model of the area of interest to provide an updated 3D model of the area of interest. The method 100 includes at step 125, based on the pathology result, updating an indicator associated with the section location of the tissue removal in the representation of the area of interest displayed on the head-mounted display device to provide an updated representation of the area of interest. Steps 115 to 125 can then be repeated throughout the surgical operation so that the representation of the area of interest can be updated based on additional pathology results of additional removed tissue. The updated representation, for example, can guide a surgeon in tracking and determining the margins of a tumor. At step 127, the updated 3D model can be converted to one or more DICOM image files that are geo-tagged or otherwise overlaid with the pathology results The DICOM image files with pathology results can be stored and used to guide postoperative treatment and/or monitoring.

Figure 2:
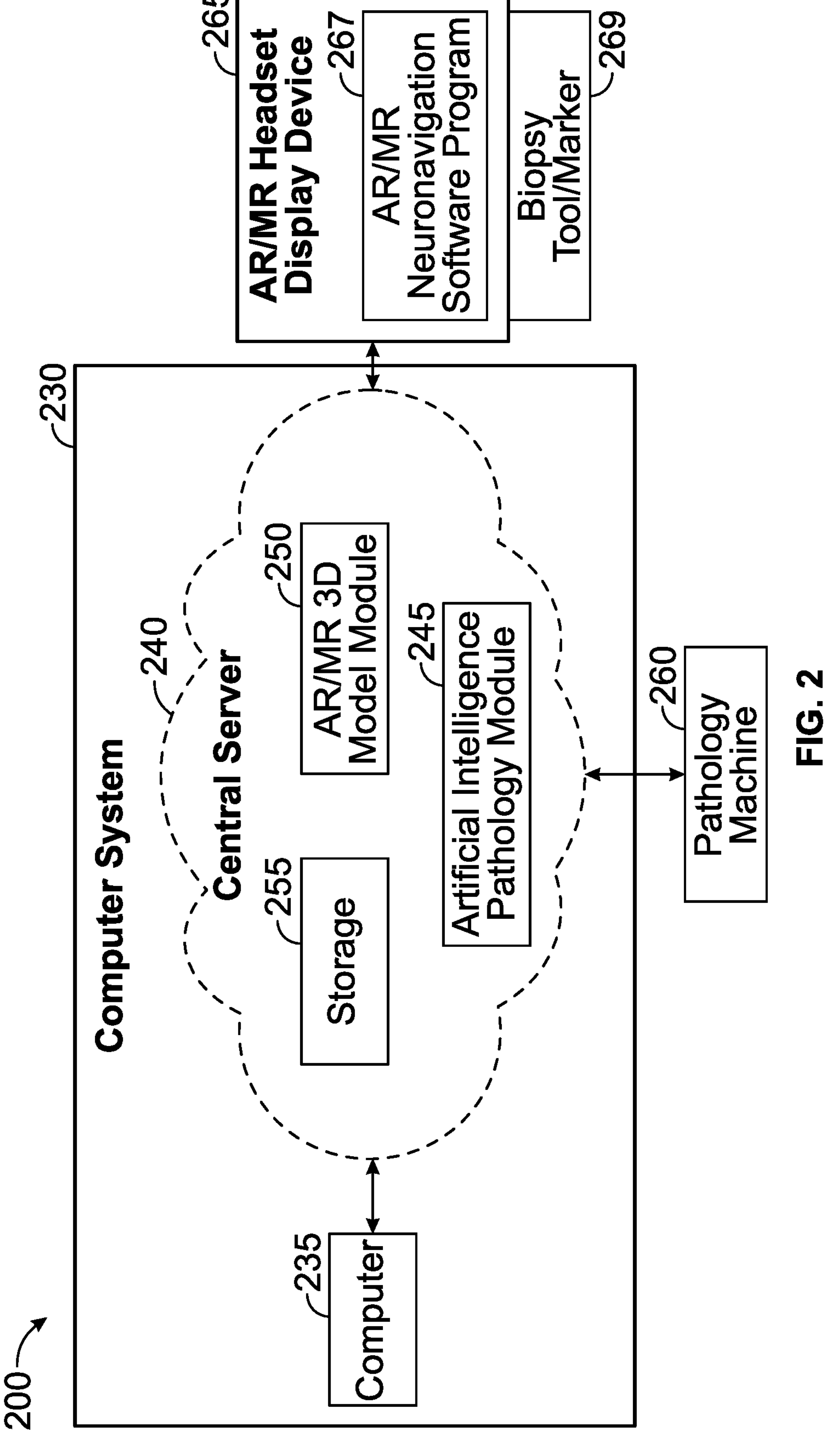
FIG. 2 is a schematic illustration of an exemplary apparatus or system for providing intraoperative surgery guidance, as well as postoperative guidance, in accordance with some embodiments

In an embodiment, as shown in FIG. 2, an apparatus 200 for providing intraoperative surgery guidance, as well as postoperative guidance, generally includes a computer system 230, which may, for example be an integrated network of computers, servers, and/or processors. As illustrated in FIG. 2, the computer system 230 includes one or more computers 235, for example, computers which may be accessed by clinicians at a hospital. The computers 235 can communicate with a central server 240 which includes, at least, a storage component 255 for storing data such as patient data (e.g., medical records, 2D and 3D imaging files), programs, and program instructions. The central server 240 further includes, at least, an augmented reality/mixed reality 3D model module or program 250 and, in the illustrated embodiment, an artificial intelligence pathology module 245. The apparatus further includes an augmented reality/mixed reality (AR/MR) display device 265, for example, a headset, which includes an augmented reality/mixed reality navigation software program 267 (for example, a neuronavigation software program). The apparatus may include a biopsy tool or marker 269 for marking a location of a tissue removal from a patient in an augmented reality/mixed reality 3D model during a surgical operation, and, in some embodiments, for also removing the tissue. The central server 240 is operable to communicate with and perform a process associated with the augmented reality/mixed reality display device 265, and is further operable to communicate with and perform a process associated with a pathology machine 260 which provides pathology results for the tissue removals.

Figure 3:
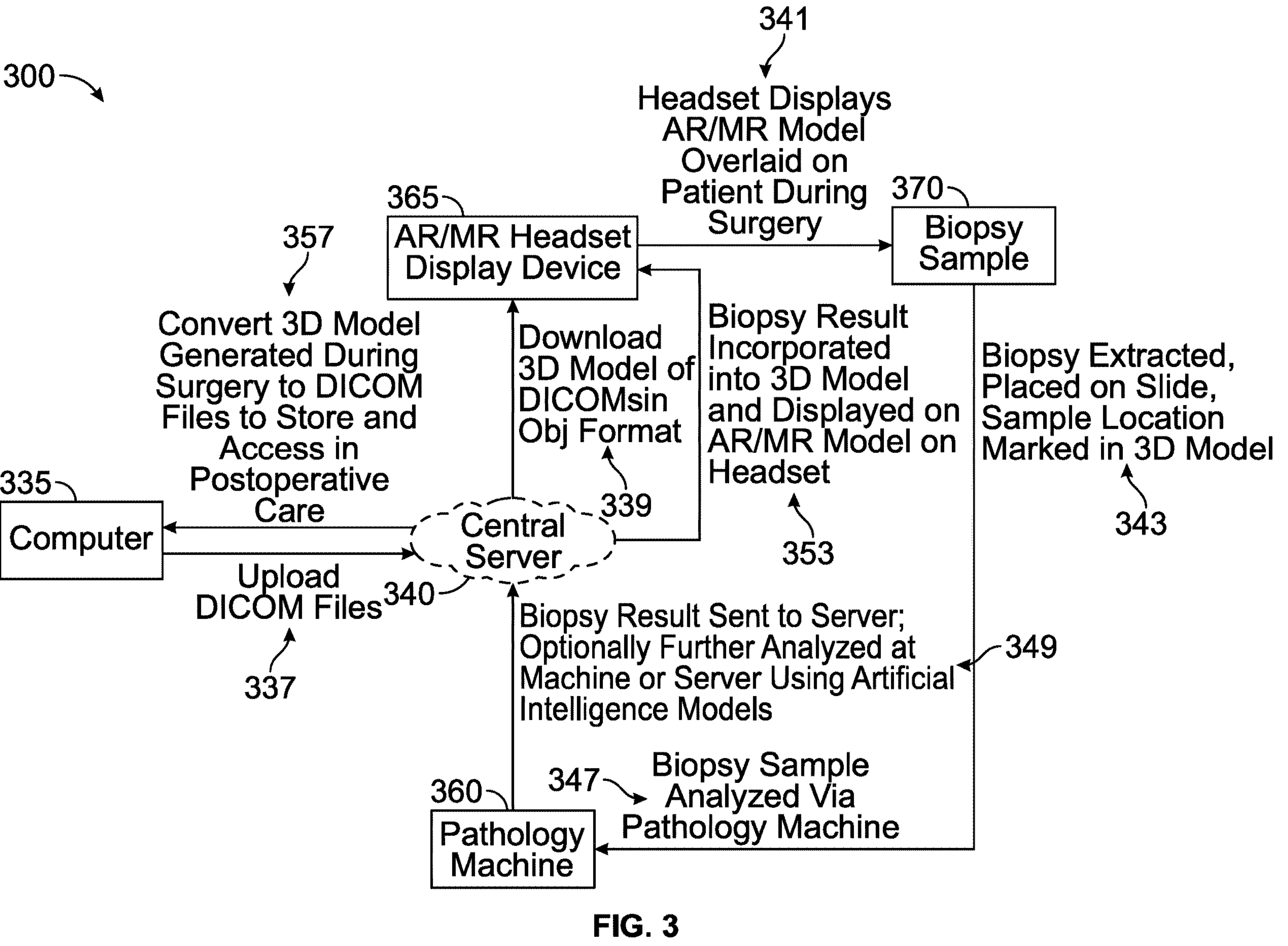
FIG. 3 is a schematic diagram depicting an apparatus and method for using augmented reality and near real-time pathology results in surgical settings, in accordance with some embodiments.

In an exemplary embodiment, as shown in FIG. 3, a method 300 is performed via an integrated network that includes, at least, a computer 335; an augmented/mixed reality device 365, including augmented/mixed reality software and hardware, operable to generate and display a 3D model of a patient's anatomy in a surgical field to a user of the device; a pathology machine 360 operable to rapidly determine pathology results of patient tissue samples using artificial intelligence, wherein the pathology results are used to update the 3D model during surgery; and a central server 340 operable to store data, programs, and program instructions, communicate with the augmented/mixed reality device 365 and pathology machine 360, and perform a process associated with the augmented/mixed reality device 365 and pathology machine 360.

As shown in FIG. 3, the method includes uploading preoperative imaging files such as DICOM files 337 associated with a patient to the central server 340 from one or more computers 335. The preoperative imaging files 337 can be accompanied by other data relating to the patient, such as medical records, diagnostic information, pathology information, and other clinical or demographic information. These preoperative imaging files may be DICOM files including radiology imaging modalities such as CT (computed tomography), PET (positron emission tomography), MRI (magnetic resonance imaging), X-ray, and ultrasound along with a set of metadata. The imaging files include images of an area of interest of the patient's anatomy, and, particularly, an area of interest that will undergo a medical procedure or operation, such as a tumor.

The central server 340 may then be configured to enable conversion of the DICOM files into a 3D model which is then 339 downloaded onto an AR/MR display device 365. For instance, the DICOM images may be converted into one or more files that can be recognized by software on an AR/MR device 365 (for example, in OBJ format). In an exemplary embodiment, the files are consolidated into one 3D object or model rather than separate images, and may represent an area of interest of the patient's anatomy. By an alternative approach, the conversion may occur via a program on the computer 335.

The AR/MR device 365, such as an AR/MR headset, may be operable to receive or download the 3D model converted from the DICOM images, such as from the computer 335 or the central server 340, and subsequently generate an augmented reality/mixed reality 3D model of a patient's anatomy based on the 3D model. For example, the AR/MR device may receive or generate a 3D model of the DICOM images in OBJ format and generate an augmented reality/mixed reality model or representation based on the 3D model file. During surgery, the generated augmented reality/mixed reality representation, which, for example, can include a rendered model of a tumor to be excised, can be 341 displayed superimposed on the patient's body in the surgical field, and is configured to provide accurate, continuous, real-time anatomical visualization and navigation as the surgeon operates.

In exemplary embodiments, the augmented/mixed reality device 365 includes an augmented/mixed reality wireless headset such as the Microsoft HoloLens 2 and runs a software application suitable for neuronavigation in cranial neurosurgery. When a user wears the augmented/mixed reality headset 365, the software application generates a 3D model or representation to appear superimposed over the patient, visible to the user of the device. For example, a 3D model of a patient's brain or a portion thereof (e.g., investigation area, markers, estimated tumor margin) generated from preoperative medical images may be superimposed over the patient's head. The 3D model remains fixed in location over the patient's head even if the headset wearer moves around the room and changes the angle of sight. As no navigation wand is required, neuronavigation and visualization is hands-free. Further, a surgeon's attention and line of sight are preserved during surgery, as the 3D model is projected precisely onto the surgical field, instead of being located on a separate monitor elsewhere in the operating room.

The software application running on the augmented/mixed reality headset includes functionalities suitable for visualizing and navigating a patient's anatomy during surgery. For example, a user can "fly" through the anatomical model, by switching between different views and layers of the anatomy. In addition to 3D viewing, the user may also view 2D images of various slices of the rendered model. The image plane can also be changed to the axial, coronal, or sagittal plane. The rendered models may also include overlays of markings or other information as a result of preoperative planning, such as emphasizing certain structures to avoid, or indicating potential tumor margins. Further, the AR/MR device allows a user to interact with the software menus and navigation via hand gestures and voice detected commands. Further advantageous functionalities of the software, such as marking and geotagging a pathology sample and updating the model based on pathology results, will be described below.

The rendered 3D model is registered to the anatomical area of interest of the patient so that the 3D model is accurately aligned with its physical counterpart within 2 mm. This ensures that the model can provide accurate intraoperative guidance as the surgeon performs a procedure on the area of interest of the patient. For instance, in tumor excision, the fiducial registration error (FRE) should be less than 2 mm so that expected tumor borders can be accurately traced as tumor is removed. The registration can be performed in accord with any known manual and/or automatic processes in the art that provide this level of accuracy. For example, a registration process may involve point-matching of virtual and real spaces using known or rigid anatomic landmarks such as nose and ears. For instance, at least five surface points including the eyes, ears, and nose can be used to align and verify the accuracy of the alignment of the 3D model with the physical area of interest on the patient. The software application of the AR/MR device, in some embodiments, detects hand gestures which are used to move and manipulate the 3D model until it lines up with the patient's facial anatomy. Remote servers leveraging AI algorithms for facial recognition such as Microsoft Azure can also be used to automatically provide accurate alignment.

As shown in FIG. 3, the method 300 further communicates with a pathology machine operable to determine pathology results of tissue samples collected during the surgery so that the rendered 3D model can be updated with the pathology results intraoperatively. For instance, during surgery a tissue or biopsy sample 370 may be 343 extracted and placed on a slide. As discussed in further detail below, the location the tissue sample 370 was extracted from may be marked in the 3D model. The biopsy sample 370 is then 347 analyzed for pathology characteristics, such as via pathology machine 360 and the results are sent 349 to the central server 340. Preferably, the pathology machine is on-site ad analyzes one or more biopsy samples 370 and provides pathology results rapidly, in order to provide actionable guidance to the surgeon while the surgery progresses. The pathology result may simply indicate absence (negative) or presence (positive) of a pathology characteristic such as cancer, or may include one or more pathology values or scores. For example, a pathology score may include a probability of cancer presence, a probability of cancer recurrence, and/or a time to cancer recurrence associated with the tissue sample 370.

In an advantageous embodiment, the pathology machine utilizes Stimulated Raman Histology (SRH) to process the specimens collected from the surgery. SRH is a non-destructive, rapid, label-free pathology technique that provides imaging of unprocessed surgical tissues at microscopic resolutions. SRH has been found to characterize tumorous and non-tumorous tissues with excellent sensitivity and specificity, and can do so significantly faster than conventional pathology methods such as frozen section analysis, as explained in the journal article D. G. Eichberg et. al., "Stimulated Raman histology for rapid and accurate intraoperative diagnosis of CNS tumors: prospective blinded study", Journal of Neurosurgery, Vol. 134:1, Dec. 6, 2019, pp. 137-143; the contents of which are incorporated by reference herein.

In a preferred embodiment, the pathology machine 360 and/or the central server 340 further uses artificial intelligence to automatically analyze the samples 370 and provide a pathology result for each sample in near real-time. An exemplary machine is the commercially available NIO Laser Imaging System (Invenio Imaging), which can be used directly in the operating room. The NIO automates SRH image analysis with machine learning algorithms, further accelerating the process and minimizing the risk of misdiagnosis due to human error. A streamlined and efficient workflow for intraoperative diagnosis is thus provided, as the workflow is not dependent on consultation with a traditional pathology laboratory. Preferably, a pathology result for a sample is provided from a pathology machine back to the operating room (e.g., displayed in the augmented/mixed reality model overlaid on the patient) in less than three minutes, more preferably in less than one minute, and even more preferably in about 30 seconds or less.

Use of a SRH pathology machine with artificial intelligence, as described above, is particularly advantageous during resection surgeries because it can quickly and accurately convey integral pathology information to a surgeon when the surgeon is assessing tumor margins. Because tumorous tissue can be diffuse with an infiltrative margin, the boundaries of a tumor often cannot be precisely determined from a small set of pathology samples. The above-mentioned machine, however, can feasibly run a large set of samples from the tumor margins in a short period of time during surgery to provide a more complete picture of where tumor residual lies. Accordingly, use of an SRH pathology machine with artificial intelligence contributes to a more precise intraoperative determination of safe tumor margins and thereby enhances extent of resection.

In the embodiment illustrated in FIG. 3, a biopsy or pathology result is 340 received by the central server 340 which may store the biopsy result, incorporate the biopsy result into a 3D model of an area of interest on a patient, and/or transmit the biopsy result to the AR/MR device to update an augmented/mixed reality representation displayed over a patient while surgery is ongoing. The biopsy result can also be further analyzed. As noted above, the pathology machine 360 itself may analyze biopsy imaging using artificial intelligence before outputting a biopsy result. However, this sort of analysis, as well as further analysis, can also be conducted via the central server 340 or another processer in an integrated network or computer system.

For instance, the pathology machine 360 or the central server 340 may include a first machine learning model that examines and analyzes high resolution digital pathology images (e.g., SRH images) of the pathology samples 370 from a patient to provide a pathology diagnosis or histological information about the sample. For instance, one or more pathology values or scores may be determined through the machine learning model, such as a probability of cancer presence, probability of cancer recurrence, and/or a time to cancer recurrence associated with the pathology sample 370.

A second machine learning model may also be used that analyzes the imaging data and pathological data for the sample 370 in view of the patient's demographic and clinical data (such as, for example, age, ethnicity, clinical history, gender, nutrition, ethnicity, trauma, past surgeries, geographic data, etc.) to determine pathological, diagnostic, or prognostic information associated with the sample. For instance, the model may include as input the patient's demographic and clinical data and, in some embodiments, the 3D tumor model generated and updated by the system intraoperatively, and may output a percent probability of cancer presence, recurrence, and/or time to recurrence associated with the sample 370. Such a machine learning model may also update a percent probability of cancer recurrence or time to recurrence for the patient as a function of the patient's data and all of the biopsy samples 370 taken and analyzed during the procedure.

In some embodiments, the machine learning models may be trained by receiving pathology imaging files and data (including patient outcomes) from numerous patients over time. As the system encounters more patients and data, the machine learning models increase in accuracy in determining or predicting cancer presence, cancer recurrence, and time to recurrence at specific biopsy locations based on a patient's intraoperative imaging and pathology data and based on a patient's clinical and demographical information. In some embodiments, the machine learning algorithms output the pathology determinations or predictions in near real-time, such as in less than three minutes, less than two minutes, or in less than one minute.

The method 300 further includes 353 incorporating the pathology results into the 3D model of an area of interest on the patient. The 3D model incorporating the pathology results may be stored by the central server 340 and made available for both intraoperative and postoperative access. For instance, in postoperative care, the 3D model may be 357 converted to DICOM files of a patient's area of interest that are overlaid, embedded, and/or geo-tagged with the pathology results attained during surgery at the locations of the tissue removals associated with the pathology results. Such files can be accessed on a computer 335 to guide care and treatment of a patient post-surgery. The files may also be correlated to additional postoperative images to help identify areas of disease progression.

The 3D model incorporating the pathology results is also used to update the augmented reality/mixed reality representation overlaid on the patient during surgery to provide intraoperative guidance. The updating of the augmented reality/mixed reality representation may proceed iteratively throughout the surgery as tissue samples 370 are removed and processed for pathology results. Advantageously, the above-mentioned pathology machine, central server, and AR/MR device are integrated to provide an efficient surgical workflow and process in which pathology results are precisely mapped onto the rendered 3D model as the surgery proceeds. The resulting dynamic visual guidance is particularly advantageous for tracking and determining tumor margins.

Figure 6B:
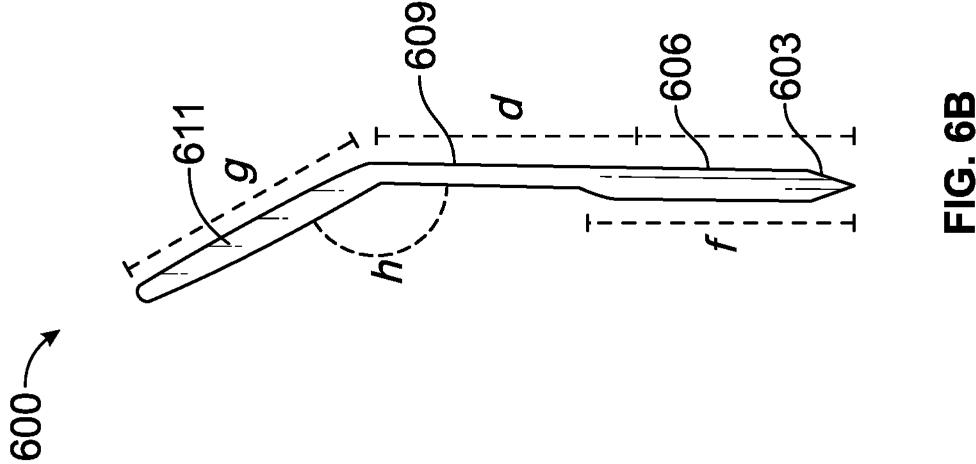
FIG. 6B is a side view of a biopsy tool, in accordance with some embodiments.
Figure 6A:
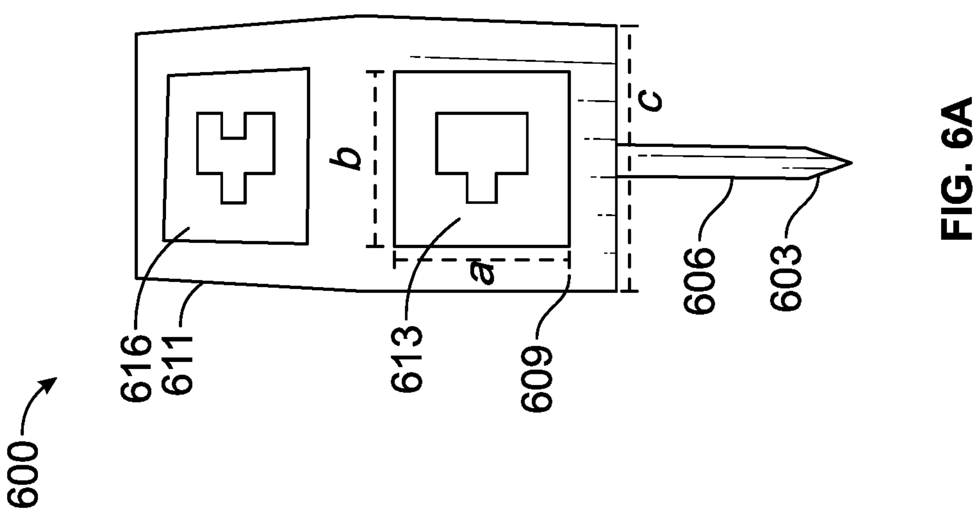
FIG. 6A is a front view of a biopsy tool, in accordance with some embodiments.

For example, in a preferred embodiment, the AR/MR device is operable to communicate with the central server in a sample-collecting process. The AR/MR device interacts with a specially designed and novel tool that serves both the function of a stylus to pinpoint biopsy locations and the function of a surgical sampling tool (biopsy tool) to physically lift the tissue sample off the patient's brain and transfer it to the biopsy slide. An example of such a tool is illustrated in FIGS. 6A and 6B. The tool 600 is held by the surgeon and includes a lower portion 606 for removing a tissue sample and marking the location of the tissue sample in the rendered augmented reality/mixed reality representation. For instance, as a stylus tip 603 points to the location of the tissue removal, one or more markers or visual/optical codes or identifiers 613, 616 (e.g., QR codes) attached to the tool 600 at one or more upper portions 609, 611 of the tool 600 may be configured to be in the line of sight of sensors on the augmented reality headset and provide geolocational information to the AR/MR device. For example, the position of the tool tip 603 may be obtained by a trigonometry calculation based on the position of one or more of the QR codes when they are scanned or read by the sensors. The sample location is then marked with a 3D marker in the rendered augmented reality/mixed reality representation displayed by the AR/MR device, and a correspondence is made with the exact same location on a stored 3D model and/or on a 2D DICOM scan, which is also marked accordingly.

In the illustrated embodiment, the tool 600 includes two different QR codes 613, 616 in a stacked or vertical arrangement. Specifically, a first QR code 613 is adjacent to the lower portion 606 of the tool 600, and both the first QR code 613 and the lower portion 606 are aligned on a first plane, while a second QR code 616 is disposed adjacent to and above the first QR code 613 on a second plane that is angled with respect to the first plane. Thus, the first QR code 613 and the second QR code 616 are angled with respect to one another. Having two or more QR codes in an angled arrangement is advantageous since lighting conditions and reflections on the QR codes can sometimes render one of the QR codes unreadable during the surgery. Codes at different angles on the tool provide a backup for one another in case one of the codes cannot be quickly scanned in the current conditions. The angle h between the QR codes 613, 616 can be any suitable angle that permits optimal scanning of at least one of the QR codes in different lighting conditions by the AR/MR device. For instance, the angle h may be about 130 to about 160 degrees. In an exemplary embodiment the angle h is about 150 degrees. The tool 600 may also have QR code dimensions a and b, for example, about 40 mm by about 40 mm, that enable the QR codes to be scanned without largely obscuring the surgeon's view of the patient. The dimensions of the upper portions 609, 611 may also follow this principle, for example, being about 60 mm by 60 mm each (e.g., c being about 60 mm and g being about 60 mm). The lower portion 606 may have a measurement f of about 60 mm and the tool 600 may have a length d of about 80 mm from the tip 603 to where the angled portion begins.

Figure 5A:
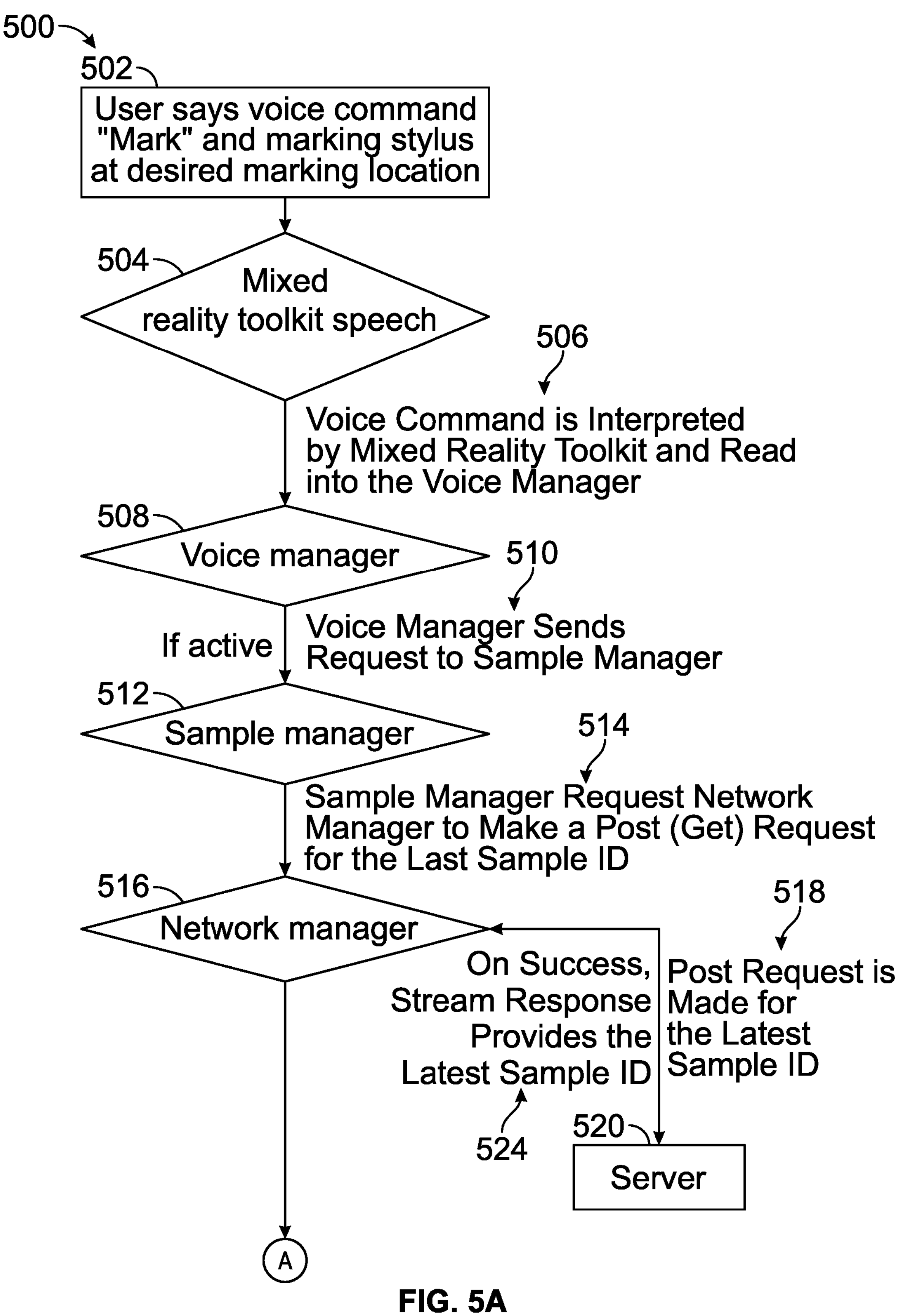
FIG. 5A is a first portion of a schematic diagram depicting a process in which software modules of an augmented/mixed reality device and the central server perform a process associated with collecting and marking a pathology sample, in accordance with some embodiments.
Figure 5B:
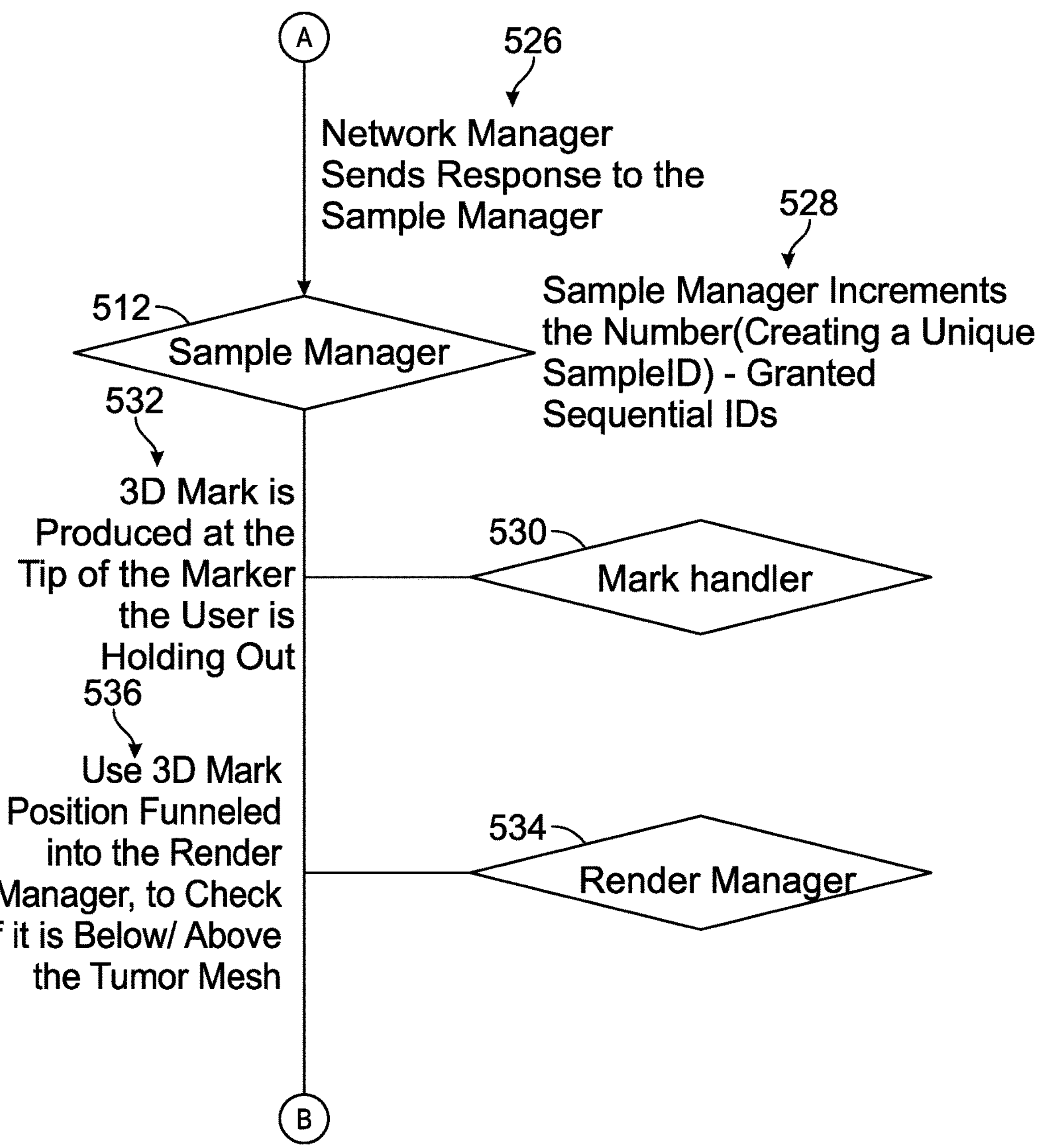
FIG. 5B is a second portion of a schematic diagram depicting a process in which software modules of an augmented/mixed reality device and a central server perform a process associated with collecting and marking a pathology, in accordance with some embodiments.
Figure 5C:
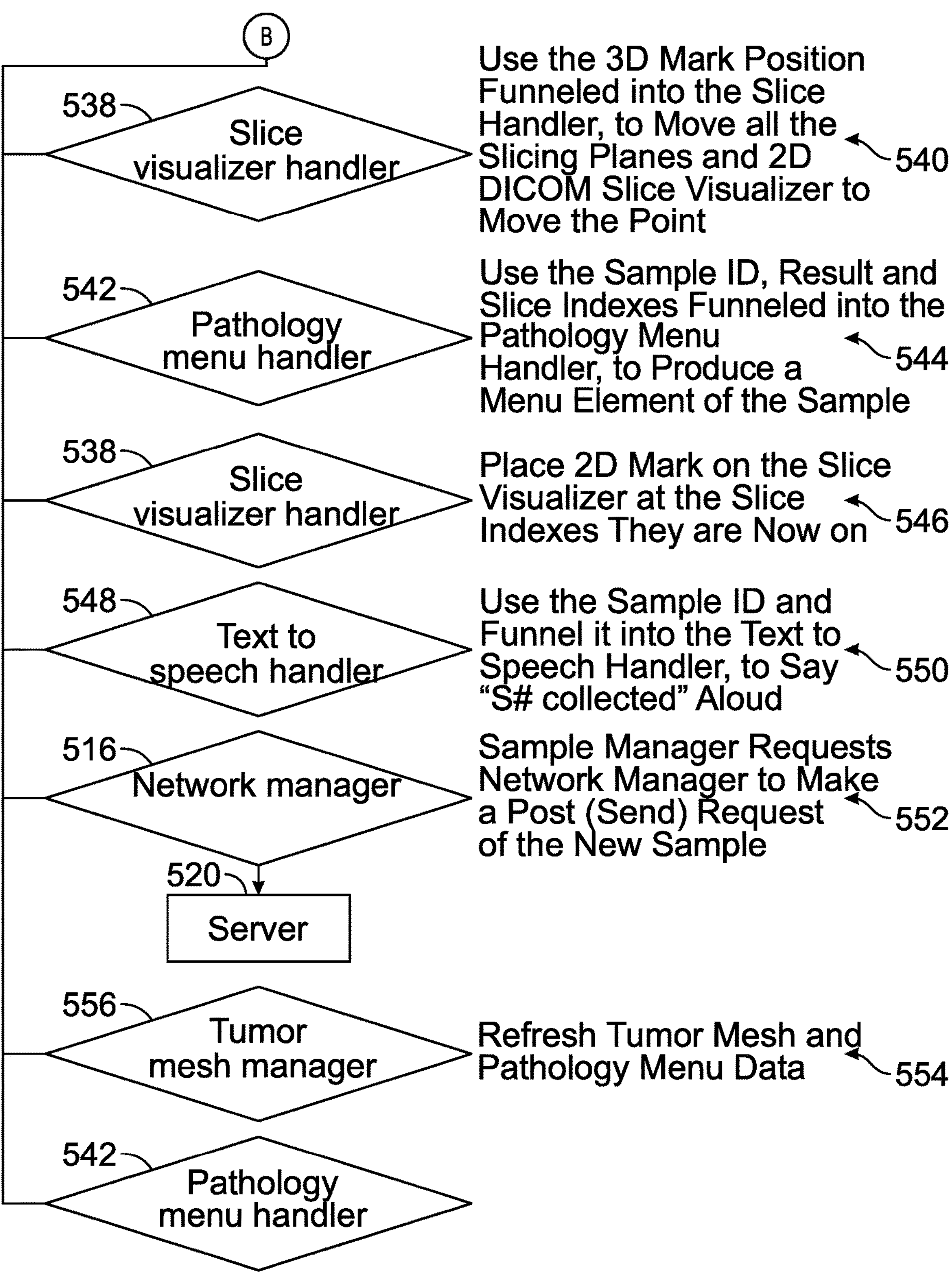
FIG. 5C is a third portion of a schematic diagram depicting a process in which software modules of an augmented/mixed reality device and a central server perform a process associated with collecting and marking a pathology, in accordance with some embodiments.

Further details of an exemplary software process 500 that occurs during sample-collecting are illustrated in FIGS. 5A-5C. Generally, the schematic diagram illustrates a manner in which software modules running on an AR/MR device and/or the central server may perform a process associated with collecting and marking a pathology sample.

For instance, at 502, a starting point of the process may occur when 502 a user, e.g., a surgeon who is removing a tissue sample during surgery for pathology analysis, says a voice command such as "mark" while holding a marking tool (e.g., tool 600 described above) at the location of the tissue sample. A Mixed Reality Toolkit Speech module 504 subsequently 506 interprets the voice command and engages a Voice Manager 508 which 510 sends a request to the Sample Manager 512. In some embodiments, the tissue removal is detected via a predefined motion by the user. For example, the user may perform a tapping or double tapping motion with the tool 600 that is detected via an optical sensor on the head mounted display or another optical device. The Sample Manager 512 then 514 requests the Network Manager 516 to make a request for the last sample ID in order to determine a current sample ID for a current sample. The Network Manager 516 then proceeds to request 518 the latest sample ID from the central server 520, which 524 provides the latest sample ID to the Network Manager 516. A response is then sent back 526 to the Sample Manager 512, which creates 528 a unique sample ID for the current sample.

At 532, via a Mark Handler module 530, a 3D mark or marker is produced at the tip of the marking tool in the augmented/mixed reality representation overlaid on the patient. The 3D mark, for example, may be spherical with a diameter of about 2 mm, and may initially be displayed with a color to indicate that pathology results have not yet been received for the sample. A Render Manager 534 can then 536 use the 3D mark position to check if the mark is below or above the mesh of a virtual representation of a tumor to provide an accurate rendering. The representation of the tumor is adjusted according to whether the position of the sample is above or below the mesh. For example, if the marked position of the sample is above the mesh, the tumor margin will be adjusted upwards, and if the marked position of the sample is below the mesh, the tumor margin will not be adjusted. Therefore the mesh will always be a representation of the outer most boundary of the resection.

A Slice Visualizer Handler module 538 additionally functions to use the 3D mark position to update 540 the slicing planes (sagittal, coronal, axial). The Slice Visualizer Handler module 538 also 546 associates 2D marks representing the position of the tissue sample with different slices. The Slice Visualizer Handler 538 includes lists for marked point locations where the 2D marks are stored, and the 2D marks are revealed when a user selects to visualize a specific corresponding slice index.

At 544, the sample ID, a result index, and slice indexes are funneled into a Pathology Menu Handler module 542 to produce a menu element for the sample. Menu items display the same ID, any user-made description, pathology results for the sample, and slice indexes for the sample. The menu item may include color-coding to indicate the severity of the pathology result for the sample after it is received. The color-coding, for instance, can depend on preset thresholds set by the user (e.g., green could be 0-25% probability of cancer, yellow could be 25-75% probability of cancer, red could be 75-100% probability of cancer).

At 550, the sample ID is funneled into the Text to Speech Handler module 548 which indicates aloud that the sample is collected. The Sample Manager 512 subsequently requests 552 the Network Manager 516 to make a request with respect to the central server 520 with respect to the sample. When pathology results are received for the sample, at 554 the tumor mesh is updated via the Tumor Mesh Manager 556 and the pathology menu data is updated via the Pathology Menu Handler 542.

Generally, the AR/MR device is operable to communicate with the central server and update the augmented/mixed reality representation overlaid on the patient by incorporating near real-time pathology results for the collected samples into the representation so that tumor margins can be visualized more precisely during the surgery. The application thus renders a dynamic 3D model of the tumor, which is updated based on the near instantaneous pathology results. Specifically, after the 3D coordinates of the tissue sample are stored at the time of tissue sampling, data from the pathology machine, or other point of care medical devices, can then be delivered to update the status of this virtual point with new medical information in real-time. By one approach, the tumor margin is updated to reflect a positive (red) or negative (green) pathology result at each virtual point corresponding to each sample taken. That is, the pathology result of the sample is incorporated into the tumor model. Because samples are typically taken at the tumor margin, to help surgeons identify the area to be resected, the application helps the surgeon redefine this area in real time by re-drawing the margin every time a sample is taken. An optimal end result of a completed surgery would be a tumor model having a margin entirely defined by green samples, which suggests that all tumorous tissue has been removed. If the end result of a completed surgery has positive margins this would indicate residual tumor, and the data points and associated pathology information would be stored and used to guide further intraoperative or postoperative therapy such as radiation or focused ultrasound.

An exemplary method 400 of updating a virtual model of a tumor based on intraoperative pathology results is illustrated in FIG. 4. The process begins with marking the location of a collected sample collected from a potential tumor margin, and subsequently updates the surface boundary and mesh of a tumor model depending on the location and pathology result of the sample.

As illustrated in FIG. 4, at 470 coordinates of a marked point indicating the location of a tissue removal/biopsy sample in a 3D model of an area of interest on a patient are sent to a central server. The coordinates may be determined via an interaction between sensors on an AR/MR headset device and a biopsy stylus or tool, such as the biopsy tool 600 described above. In one example, when a location is being marked and/or when a sample is collected, the user may make a voice command (e.g., "mark") and the system would register the 3D location of the biopsy tool tip at the time the voice command is made. Other methods of indicating the marking of a location to the AR/MR device or server may also be used. The marked point is represented by a 3D marker in a neutral color (e.g., gray) in an augmented/mixed reality representation of the area of interest overlaid on a patient during surgery.

At 475, the server outputs a pathology result for the biopsy sample to the AR/MR headset device. At 480, the marked point in the 3D model of the area of interest is updated with the pathology result and the marker associated with the biopsy sample in the AR/MR representation displayed on the patient is updated based on the pathology result. For instance, the 3D mesh may be updated to add a data point at the marked point that includes the pathology result of the sample collected at the marked location. For example, the 3D mesh may be stored as a set of data points each represented by a 3D coordinate and a pathology value indicating the likelihood or confidence level that the sample collected at the location is cancerous. The 3D coordinate may be a relative coordinate anchored to a reference point.

In some embodiments, each marked point on the 3D mesh representing the tumor mass and/or margin may be color-coded based on the pathology value in the AR/MR display. The color-coding may be based on thresholds preset by the user. For example, red may correspond to a high pathology value (e.g., likely cancerous) and green may correspond to a low pathology value (e.g., likely normal tissue). By one approach the pathology result includes a pathology score. The pathology score, for instance, could be a percent probability of cancerous or tumorous tissue in the sample, a percent probability of cancer recurrence associated with the sample, or a time to cancer recurrence associated with the sample. These scores or percentages can be provided by the central server as an output of the machine learning models described above, and can be reflected in the virtual space through color-coding. For instance, scores in different ranges could be set to be associated with different colors, and the markers could be color-coded based on the scores so that a clinician can easily see which portions of the area of interest to focus on (e.g., which areas require further excision). In addition, the pathology data, for example, the percent probability of tumor, may also be displayed over each marker in virtual space.

After the pathology result of the collected sample is received and used to update the marker on the augmented reality/mixed reality display, the surface of the 3D model of tumor is updated 485. For every marked point that is to be updated with a pathology result, lists in a Slice Visualizer module are updated. These indicate the points that are on the surface of the shape of the model so that the shape of the 3D model of the tumor can be updated. At 490, starting from points on the surface of the determined shape, triangles are created to form an updated 3D mesh of the tumor. As illustrated in FIG. 4, the entire process of updating the tumor mesh based on pathology results associated with specific locations repeats as new tissue samples are taken and analyzed.

During an operation, the surface boundaries and mesh of the rendered tumor model are continuously updated as more samples are removed, based on the location of the markers and the corresponding pathology results. The model depicts the area of the tumor that has already been excised and indicates to the operator what additionally may need to be excised. For example, an operator may decide to continue to remove tissues under markers indicated with high pathology values (e.g., red) to ensure a more thorough removal of cancerous tissue while stopping the removal in areas marked with low pathology values (e.g., green). In some embodiments, the displayed AR/MR image may only include the data points at the margin of the tumor mass, which corresponds to locations adjacent to the surface of the remaining tissue. Visualizing and tracking the boundaries of a tumor in this manner, a surgeon is guided in excising further tissue and determining appropriate margins.

The central server is further operable to store pathology sample results and their marked locations so that they can be accessed or downloaded at a computer web portal. In a further aspect, the pathology results accessed or downloaded from the central server are received as imaging files, such as DICOM files, including a geolocational overlay of the pathology results, or otherwise embedding the pathology information into the files. These images can be referenced by doctors and provide postoperative guidance, for example, in determining more precise intraoperative or postoperative adjuvant therapy, and may also be correlated with additional postoperative imaging files for the patient to track disease progression. The 3D and 2D image data may also be used to control radiotherapy devices to define the area of treatment to assist radiologists with identifying future tumor progression. For instance, radiation may be focused on areas of concern identified by geotagged pathology information generated at the time of surgery.

As noted above, in some embodiments, the central server is further configured to predict other pathology information such as chance of recurrence and/or time to recurrence at each marked location of the 3D model or for the patient and provide that information for display via the augmented/mixed reality device or through a web portal. In some embodiments, the central server may train a machine learning model using patient demographic information, medical history, tumor characteristics, and/or pathology analysis as input and long-term outcome (e.g., chance of recurrence) as categorization. The server may then associate the additional information from the machine learning algorithm to each marked location of the 3D model. The predictive information may be displayed on the AR/MR model projected during the operation to aid in intraoperative decision-making and/or provided via the web portal to persons administrating post-operative treatment.

While the system is generally described as including an augmented/mixed reality device and a server each performing separate functions, in some embodiments, the augmented/mixed reality device may perform one or more functions described as a server function here and vice versa. For example, the augmented/mixed reality device may be a thin client that only collects data and displays images with minimal processing. In another example, the augmented/mixed reality device may communicate directly with the pathology machine and update the displayed 3D model with pathology indicators without an active connection to the server. The 3D model with pathology information may be uploaded to the server periodically or upon completion of the operation.

A method for using augmented/mixed reality in surgical settings, in particular a method in which pathology results are incorporated into augmented/mixed reality 3D models to guide surgery, is also provided. The method includes providing preoperative information including medical imaging files and other data relating to a patient to a central server, and providing the information to an augmented/mixed reality device that uses the information to generate an augmented/mixed reality 3D model of a patient's anatomy overlaid on the patient's body and registered thereto, which provides accurate, continuous, real-time anatomical visualization and navigation as a surgeon operates. Further steps comprise collecting a tissue sample from a location; marking the location of the sample in the augmented/mixed reality model; providing the tissue sample to a pathology machine which determines a pathology result using artificial intelligence and provides the pathology result to the central server; receiving the pathology result from the central server at the augmented/mixed reality device; and intraoperatively updating the augmented/mixed reality model with the pathology result. The method may further include storing the pathology result and marked location on the central server and accessing or downloading the pathology results on a web portal. In a further aspect, the pathology results accessed or downloaded from the central server are received as imaging files having a geolocational overlay of the pathology results, and the method includes a step of using the files to guide postoperative therapy.

Further provided is a method for precisely determining and recording tumor margins in a resection surgery through use of augmented/mixed reality incorporating near real-time pathology results. The method comprises providing information including imaging files and other data relating to a patient to a central server, and providing the information to an augmented/mixed reality device which generates an augmented/mixed reality 3D model of the patient's anatomy, wherein the model includes a model of a tumor including a shape with a surface boundary, the model overlaid on the patient's body and registered thereto, and the augmented/mixed reality device providing accurate, continuous, real-time anatomical visualization and navigation as the surgeon uses the device and excises the tumor. The method further includes collecting a tissue sample at a location, preferably at a potential tumor margin; using the augmented/mixed reality device and a stylus to mark the location of the sample in the augmented/mixed reality model with a marker; providing coordinates of the sample location to the central server; providing the tissue sample to a pathology machine which determines a pathology result using artificial intelligence; providing the pathology result to the central server; receiving the pathology result from the central server at the augmented/mixed reality device; updating the 2D DICOM scans of the patient based on the location of the sample taken and its corresponding pathology result; and updating the augmented/mixed reality model with the pathology result to determine tumor margins intraoperatively by a) visually indicating the severity of the pathology result at the marker using thresholds preset by the user, and b) using the markers to update the surface boundary and mesh of the tumor model. The method may further include storing the pathology results and marked locations on a central server and accessing or downloading the pathology results on a computer web portal. In a further aspect, the pathology results accessed or downloaded from the central server are received as imaging files having a geolocational overlay of the pathology results and/or the tumor margin, and the method includes using the files to guide intraoperative and/or post-operative adjuvant therapy.

While the above-mentioned apparatus and methods are described largely with respect to cranial neurosurgery, it is contemplated that the apparatus and methods are not limited thereto. The apparatus and methods can apply to other surgical resections and types of surgery in other specialties, for example, to treat breast cancer, squamous cell carcinoma, head and neck cancer and other cancers, as well as sampling abnormal non-cancerous tissue such as inflammatory, demyelinating, infectious, necrotic, or infarcted tissue or sampling normal tissue such as bone quality during orthopedic surgery.

Uses of singular terms such as "a," "an," are intended to cover both the singular and the plural, unless otherwise indicated herein or clearly contradicted by context. The terms "comprising," "having," "including," and "containing" are to be construed as open-ended terms.

Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A method for providing intraoperative surgery guidance, comprising:

generating, with a processor of a computer system, a 3D model of an area of interest on a patient's body;

based on the 3D model of the area of interest, providing a representation of the area of interest displayed on a head-mounted display device worn by a user, the representation of the area of interest displayed as an overlay over the user's view of the area of interest through the head-mounted display device during a surgical operation, the representation including pathology characteristics associated with the area of interest;

detecting, with the processor during the surgical operation, a tissue removal and a section location associated with the tissue removal;

associating the section location with a pathology result associated with the tissue removal in the 3D model of the area of interest to provide an updated 3D model of the area of interest during the surgical operation; and based on the pathology result, updating an indicator associated with the section location of the tissue removal in the representation of the area of interest displayed on the head-mounted display device to provide an updated representation of the area of interest during the surgical operation.

2. The method of claim 1, wherein the 3D model is converted from one or more previously stored Digital Imaging and Communications in Medicine ("DICOM") files of the area of interest.

3. The method of claim 1, wherein the updated representation of the area of interest includes a plurality of indicators associated with a plurality of tissue removals, and the plurality of indicators comprise color-coding the area of interest.

4. The method of claim 3, wherein the pathology result comprises a pathology score, and the plurality of indicators are color-coded according to the pathology score associated with each of the plurality of indicators and one or more preset pathology score thresholds.

5. The method of claim 1, wherein the representation of the area of interest comprises an augmented reality and/or mixed reality display.

6. The method of claim 1, wherein the section location of the tissue removal is detected via an optical sensor tracking a position of a surgical tool.

7. The method of claim 6, wherein the optical sensor tracks a position of one or more optical codes on the surgical tool to detect the section location of the tissue removal.

8. The method of claim 1, wherein the tissue removal is detected via a predefined motion or voice command by the user.

9. The method of claim 1, wherein the pathology result is received from an on-site pathology machine configured to provide the pathology result in less than three minutes.

10. The method of claim 1, wherein the pathology result comprises one or more pathology scores including at least one of a probability of cancer presence associated with the tissue removal, a probability of cancer recurrence associated with the tissue removal, or a time to cancer recurrence associated with the tissue removal.

11. The method of claim 10, wherein the one or more pathology scores are determined through use of a machine learning model which determines the pathology scores based at least on pathology imaging files associated with the tissue removal and demographic and clinical data associated with the patient.

12. The method of claim 11, wherein the machine learning model further bases the one or more pathology scores on the 3D model of the area of interest or the updated 3D model of the area of interest.

13. The method of claim 11, wherein the one or more pathology scores are displayed on the representation of the area of interest during the surgical operation.

14. The method of claim 11, wherein the one or more pathology scores are used to identify margins of a tumor being excised.

15. The method of claim 1, further comprising converting the updated 3D model of the area of interest to one or more DICOM image files that are geo-tagged with the pathology result and using the DICOM image files to guide postoperative treatment and/or monitoring.

16. An apparatus for providing intraoperative and postoperative surgery guidance, comprising:

a computer system operable to generate a 3D model of an area of interest on a patient's body;

a head-mounted augmented/mixed reality display device to be worn by a user, for generating a representation of the area of interest based on the 3D model of the area of interest displayed as an overlay over a user's view of the area of interest during a surgical operation, wherein the representation includes pathology characteristics associated with the area of interest; and a central server of the computer system, the central server operable to:

communicate, during the surgical operation, with the head-mounted augmented/mixed reality display device to detect a tissue removal and a section location associated with the tissue removal, associate the section location with a pathology result associated with the tissue removal in the 3D model of the area of interest to provide an updated 3D model of the area of interest during the surgical operation, and based on the pathology result, update an indicator associated with the section location of the tissue removal in the representation of the area of interest displayed on the head-mounted display device to provide an updated representation of the area of interest during the surgical operation.

17. The apparatus of claim 16, wherein the section location of the tissue removal is detected via an optical sensor tracking a position of a surgical tool.

18. The apparatus of claim 16, wherein the pathology result is received from an on-site pathology machine configured to provide the pathology result in less than three minutes.

19. The apparatus of claim 16, wherein the pathology result comprises one or more pathology scores including at least one of a probability of cancer presence associated with the tissue removal, a probability of cancer recurrence associated with the tissue removal, or a time to cancer recurrence associated with the tissue removal.

20. The apparatus of claim 19, wherein the one or more pathology scores are determined through use of a machine learning model which determines the pathology scores based at least on pathology imaging files associated with the tissue removal and demographic and clinical data associated with the patient.

* * * * *